United States Patent [19]

Tari et al.

[11] Patent Number: 4,878,918
[45] Date of Patent: Nov. 7, 1989

[54] MECHANICALLY FIXED ACETABULAR UNIT FOR PROSTHESES AND IMPLANTATION DEVICE FOR FIXING IT INTO THE COTYLOID CAVITY

[76] Inventors: Gábor Tari, Harsfa u. 16, 6640 Csongrád; Zoltán Badó, Ifjuság sétány 12, 6600 Szentes; Imre Juhász, Felszabadulás u. 61/a, 6800 Hódmezővásárhely, all of Hungary

[21] Appl. No.: 2,685
[22] PCT Filed: Nov. 5, 1985
[86] PCT No.: PCT/HU85/00062
§ 371 Date: Jan. 28, 1987
§ 102(e) Date: Jan. 28, 1987
[87] PCT Pub. No.: WO86/05679
PCT Pub. Date: Oct. 9, 1986

[30] Foreign Application Priority Data

Mar. 29, 1985 [HU] Hungary ................. 1186/85

[51] Int. Cl.⁴ ................................ A61F 2/32
[52] U.S. Cl. ............................. 623/22; 606/53; 606/91
[58] Field of Search ............... 623/18, 20, 22; 128/92 Y, 92 YZ, 92 YY, 92 YK, 92 YW, 92 YT, 92 YS, 92 YV, 92 R, 92 YE

[56] References Cited

U.S. PATENT DOCUMENTS

| | | | |
|---|---|---|---|
| 2,685,877 | 8/1954 | Dobelle | 128/92 YW |
| 3,334,624 | 8/1967 | Schneider et al. | 128/92 YZ |
| 3,740,769 | 6/1973 | Haboush | 623/22 |
| 3,896,504 | 7/1975 | Fischer | 623/22 |
| 3,939,497 | 2/1976 | Heimke et al. | 623/22 |
| 4,385,405 | 5/1983 | Teinturier | 623/22 |
| 4,498,468 | 2/1985 | Hansson | 128/92 YK |
| 4,519,100 | 5/1985 | Wills et al. | 128/92 YZ |
| 4,563,778 | 1/1986 | Roche et al. | 623/22 |

FOREIGN PATENT DOCUMENTS

| | | | |
|---|---|---|---|
| 1055498 | 11/1983 | U.S.S.R. | 128/92 YW |
| 1127582 | 12/1984 | U.S.S.R. | 128/92 Y |

*Primary Examiner*—Richard J. Apley
*Assistant Examiner*—David J. Bender
*Attorney, Agent, or Firm*—Handal & Morofsky

[57] ABSTRACT

A mechanically fixable acetabular unit for hip prostheses, having a conical acetabular basket made of a tissue-compatible metal alloy, the acetabular basket (1) is provided with cutouts (3) running in the direction of the generatrix and L-shaped anchors (4) are inserted into the cutouts (3) so, as to be tilted around the geometric axis running parallel with the tangent of the mantle of the acetabular basket and in such a manner that the shorter shank of the anchors (4) is arranged at the end with a smaller diameter of the acetabular basket and on the outer end it is formed as a pointed sharp claw (7), while the thickness of the longer shank (6) corresponds substantially to the wall-thickness of the acetabular basket (1), while the length corresponds to the length of the cutout (3).

12 Claims, 4 Drawing Sheets

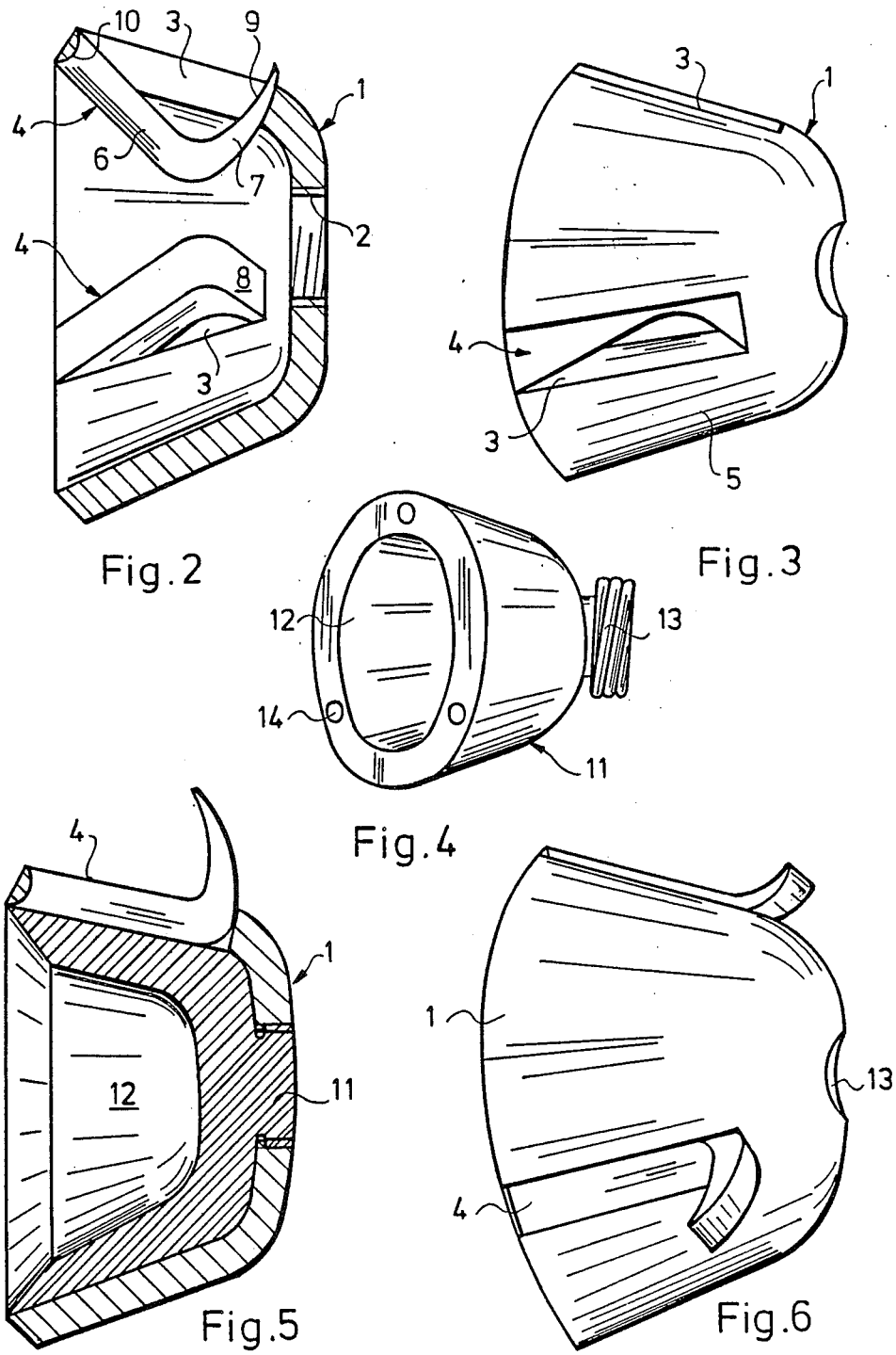

MECHANICALLY FIXED ACETABULAR UNIT FOR PROSTHESES AND IMPLANTATION DEVICE FOR FIXING IT INTO THE COTYLOID CAVITY

FIELD AND BACKGROUND OF THE INVENTION

The invention relates to an acetabular unit for prostheses, mainly for hip prostheses, which is provided with a conical basket made of a tissue-compatible metal alloy and can be anchored in the cotyloid cavity without bone cement. The invention relates also to a device for fixing said unit in the cotyloid cavity.

About four thousand prostheses, most of them hip prostheses, are implanted daily in the world. The number of implantations is ever-increasing because, as a consequence of speedy increase of average human age the number of diseases due to the wear of the joints increase proportionally. Dynamic development of surgical treatment and surrounding fields has further increased the number of implantations. At the same time, several deficiencies of the routine proceedings can be definitely outlined.

Joints are composed of two components: the spherical joint head of the neck part of the bone which is matched to the concavely shaped "counterpart" of the bone, the cotyloid cavity. Both surfaces destroyed by different pathological conditions necessitate that they be replaced. So e.g. in case of a hip-joint, the surgeon first exposes the body region and removes the head, and neckpart of the femur up to the plane between the buttocks, thereafter, he replaces the removed part with a biomechanically expediently formed prosthesis made of a tissue-compatible metal and having been chosen from a variety of different sizes and shapes of the femurs medullary cavity thus exposed. The prosthesis is fixed by a bone-cement or mechanically, thereafter, the counterpart made of a tissue-compatible synthetic material is fixed in the hollowed cavity of the hip-bone. By matching the artificial acetabular unit we obtain the ball-and-socket joint: the hip-prothesis.

Out of the most complicated partial problems accompanying the operation described above in a simplified way, one of the most frequently occuring complications to be concerned with is the loosening of the hip-acetabulum followed by the release of the whole artificial joint. Viewing the phenomenon from the point of view of biomechanics: the reasons of inadequate fixation of the prothesis, i.e. the acetabular unit and the consequent loosening thereof are due to both biological and mechanical reasons.

Biologically the problem is mainly the properties of the cementing means. Methyl acrylate is applied for this purpose, being a catalyst when polymerized at room temperature. The polimerizate is however not a complete polymer and its free monomers are tissue-destructive. At the same time it does not react at "room temperature" and exothermal heat formation may reach even 75° C., accordingly it denatures living proteins. Irrigation with a cold liquid during the course of surgical procedure is not the solution, as both the synthetic acetabulum and the acrylate are good heat-insulators. Resulting in bone destruction and the prosthetic loosening.

Mechanical problems can be explained by classical anatomic conditions: whereas the conically widening end of the tubular femur enables a relatively stable fixatin of the prosthesis, the hip-cavity is shallow and concave, as a consequence, the hemi-spherical prosthesis, which is glued-in is not as closely congruent to the anatomical site allowing it to get displaced easily under the combined effect of the shearing and compressive forces corresponding to the body weight.

Essentially the same situation must be confronted in the case of the other acetabular prostheses. It has been tried to eliminate biological deficiencies by simply omitting the bone-cement and fixing the prostheses mechanically. As previously stated, this may be acceptable for the joint-heads but is accompanied with difficulties in the cotyloid cavities.

Accordingly, experiments are carried out to eliminate said difficulties. One of the suggestions is to coat the outer surface of the metal acetabular basket embedding the acetabulum with a tissue-compatible, so-called bioactive material, which is building into the bone material and ensures mechanical anchoring.

According to another method the acetabular basket is provided with an irregular porous "bioactive" surface, into which the embedding bone surface is built-in after a certain time.

Although these solutions yield a far safer bond, when compared to earlier solutions, their fundamental drawback is that the patient post surgery is confined to bed during the long-lasting process of incorporation which may last for several weeks. Considering, that the prostheses used are usually for an elderly patient population, long confinement to bed after the surgical intervention increases considerably risks of operation pneumonia, thrombosis, decubitus ulcer etc.)

It is also known the form on the outer surface of the acetabular basket is a screw-thread or thread segments and the basket is screwed into the prepared acetabulum bed. Prior to anchoring a thread is cut in the acetabular cavity or a self-cutting formation is used.

Generally, a threaded acetabular basket is of a conical shape. Accordingly, it is unable to penetrate into the pelvis cavity. At the same time, due to its cone angle, the proper wedged state can be achieved, and compared to earlier solutions it is more resistant to tilting. However, the danger remains that it is easily torn out from the disintegrated spongy bone substance.

SUMMARY AND OBJECTS OF THE INVENTION

The object of the present invention is to provide an acetabular unit which enables mechanical anchoring of different prostheses, in particular hip prostheses, without use of bone cement. It should be implanted easily, an absolutely reliable bond could be achieved and if necessary it could be removed without difficulty.

According to the invention, the acetabular basket carrying the acetabular unit is provided with cutouts in the direction of the generatrix. Within the cutouts L-shaped anchors are inserted such that they will be tilted around the geometric axis running parallel with the tangent of the mantle of the acetabular basket. The shorter shank of the anchors should be arranged at the smaller diameter of the acetabular basket, at the same time its outer end is formed as a pointed sharp claw, while the thickness of the longer shank is equal to or less than the wall-thickness of the acetabular basket, while the length corresponds to the length of the cutout.

Preferably, the lateral walls of the cutouts are to run parallel with the radial direction, the side facing the bottom of the acetabular basket is arched, while on the face lying in direction of the opening of the acetabular basket there is an embedding trough or a rib, these are matched to the embedding rib or embedding trough having been formed on the end of the longer shank of the anchors, opposite to the end provided with the claws, to achieve easy tilting of the anchors.

With a preferred embodiment of the construction according to the invention, on the side of the cutouts facing the opening of the acetabular basket a convex cylindrical mantle segment is formed, the geometric axis of which is running parallel with the tangent of the outer mantle surface. Concurrently, in the bottom face of the longer shank of the anchors a concave cylinder mantle segment is formed, the geometric axis of which is normal to the longitudinal axis of the claw.

Expediently, the inside of the acetabular basket is also conically shaped, on the bottom there is a bore with a central thread. The acetabular unit may be provided with a central threaded pin fitting into said threaded bore.

The claws(s) on the anchors may have several edges and/or points which can be provided with ribs and/or grooves. Their bottom surface can be formed with an arc or helically.

The device for anchoring the construction according to the invention is provided with a thread on one end, fitting into the thread on the bottom of the acetabular basket. While the other end consists of a shaft having been provided with a grip. A tubular shaft fitted with a screwthread is pulled onto said shaft, while on the end of the tubular shaft facing the grip a driving wheel is arranged, while on the end fitting to the acetabular basket there is a tensioning insert with an arched or spherical surface.

The design according to the invention enables a far safer anchoring of the acetabular basket, than the solutions known up to now. The claws protruding into the bone substance are sort of pulling-in the acetabular basket into the bone cavity in course of the intrusion, while the acetabular unit arranged in the basket prevents the release of the claws. As a consequence, in course of use the acetabular basked is extremely well embedded, loosening or falling out is impossible.

Furthermore, if necessary the acetabular basket can be easily lifted out from its place, if after having removed the acetabular unit the anchors are pulled back. For this purpose in a given case the anchors may contain bore or other means.

BRIEF DESCRIPTION OF THE DRAWINGS

The invention will be described in detail by means of some preferred embodiments, by the aid of the drawings enclosed, wherein:

FIG. 2 is the sectional view of a preferred embodiment of the acetabular basket according to the invention, FIG. 3 gives the perspective view of the acetabular basket according to FIG. 2, FIG. 4 is the perspective view of the acetabular unit, FIG. 5 is the sectional view of the acetabular unit—acetabular basket construction in the assembled state, FIG. 6 is the perspective view of the construction according to FIG. 5, FIG. 7 an embodiment of the anchor, as used in the solution according to the invention.

DESCRIPTION OF THE PREFERRED EMBODIMENTS

Figure 1:
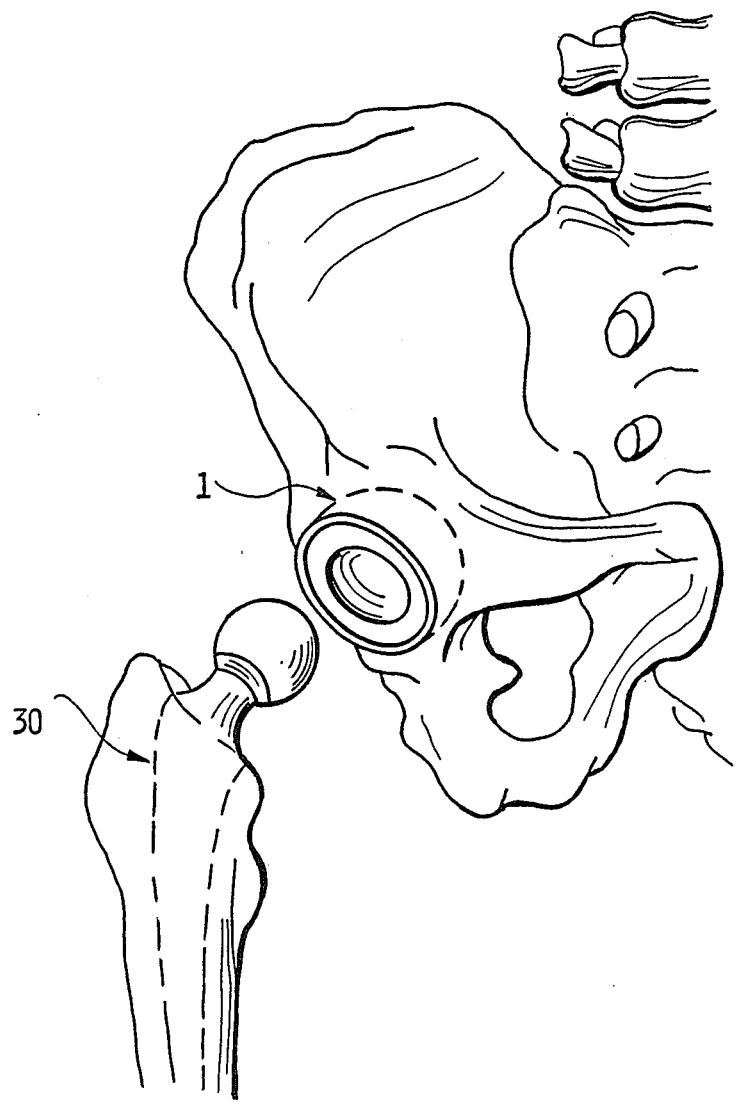
FIG. 1 shows the arrangement of the elements of the hip prosthesis in the femur, and in the hip-bone.

As it becomes obvious from FIG. 1, the hip prostheses consists two parts: of the femur part 30 to be anchored into the femur and the acetabular basket 1 implanted into the hip-bone. The present invention relates to the construction of the acetabular unit, which consists of the metal acetabular basket and of the acetabular unit anchored therein.

FIGS. 2 and 3 illustrate one of the possible embodiments of the acetabular basket according to the invention. Essentially, the acetabular basket 1 is a cup-shaped metal body having been made of a tissue-compatible alloy. The basket is conically shaped inside and outside and on the bottom part there is a central threaded bore 2. The lateral force cutouts 3—running in direction of the generatrix—are formed with the grooves 4 thereon. To increase the safety of anchoring, the outer mantle surface is provided with the ribs 5.

The anchors 4 are L-shaped and consist of a shank 6 and claw or claws 7. The upper face 8 of the claws 7 is arched, the bottom face is curved like or helically shaped.

The Side-walls of the cutouts 3 are parallel with the radial direction of the truncated cone, their upper face is arched so, as to match to the upper face 8 of the claws 7 of the anchors 4. The arch of the upper faace of the cutout 3 and the upper face of the claws 7 are formed with identical radii.

On the bottom part of the cutout 3 the embedding ribs 10 are formed, the shanks 6 of the anchors 4 are bearing up against said ribs so, that on their lower part an arched groove is formed.

In FIGS. 2 and 3 the grooves 4 occupy their basic position, that means that the claws 7 are not reaching beyond the outer mantle of the acetabular basket 1. In such a manner the acetabular basket can be easily located in the cotyloid cavity.

FIG. 4 shows another element of the construction, namely the acetabular unit 11, which may be prepared from a tissue-compatible wear-resistent synthetic material, not subjected to deformation, e.g. coalfibre-reinforced polyethylene (RCH1000). The outer mantle is fitting to the inner surface of the acetabular basket 1, its cavity 12 has a spherical surface for receiving the other element of the prosthesis, i.e. to assure articulated motion.

The acetabular unit 11 is provided with a threaded pin 13, fitting into the threaded bore 2 of the acetabular basket 1. Screwing n and out are facilitated by the bores 14 formed on the flange of the cavity 12.

FIGS. 5 and 6 illustrate the acetabular basket 1 according to FIGS. 2 and 3 anchored in the cotyloid cavity. It can be seen that the shanks 6 of the anchors 4 coincide in this position with the wall of the acetabular basket 1, while the claws 7 are extending in their full length from the mantle surface, thus anchoring the acetabular unit. The acetabular unit 11 having been screwed into the acetabular basket 1 prevents completely bending back or loosening of the anchors 4. From the position illustrated here, it becomes obvious that thickness of the shanks 6 of the anchors 4 must not exceed the wall thickness of the acetabular basket 1.

Figure 7:
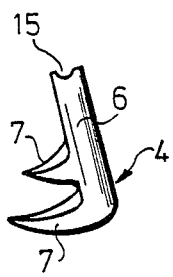

By means of the anchors 4 of the most simple construction, used with the embodiment illustrated here, anchoring of the acetabular basket can be realized with the highest safety. However, in certain cases it might be expedient to use special anchors; such special anchors are shown in FIGS. 7 to 9.

To increae the safety of anchoring, the anchor 4 according to FIG. 4 was provided with two claws 7.

Figure 8:
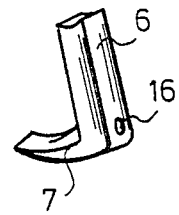
FIG. 8 shows another embodiment of the anchor.

The claw 7 of the anchor 4 in FIG. 8 has a rib on its bottom face 9, while on the outside of the shank 6 there is the profile 16 to be found which facilitates pulling back of the anchors 4, if for any reason the acetabular basket 1 is to be removed from the bone cavity.

Figure 10:
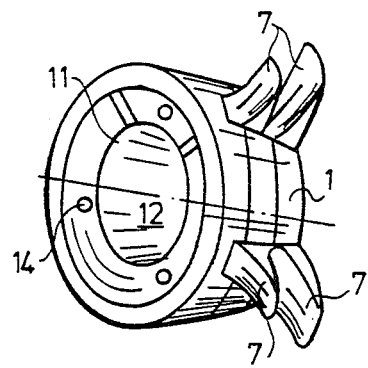
FIG. 10 is the perspective view of a version of the construction according to the invention with the anchors as to be seen in FIG. 7.
Figure 9:
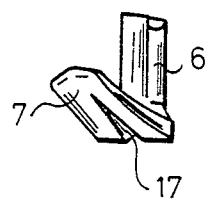

FIG. 9 illustrates a further possible embodiment of the anchor. In this case the claw 7 is relatively wide, it ends in a peak and on the upper face 8 thereof there is a groove 17. FIG. 10 presents an acetabular basket 1, which is provided with the anchors 4 with the double-claws according to FIG. 7.

It seems to be expedient, if the acetabular basket 1, as well as the acetabular unit 11 and the anchors 4 are made in different sizes, similarly to the usual prosthesis-series. Expediently, the different types of the anchors 4 can be exchanged, accordingly, in a given case the optimal version can be chosen. Additionally, in case of necessity diverse claws can be arranged within one single acetabular basket.

Figure 11:
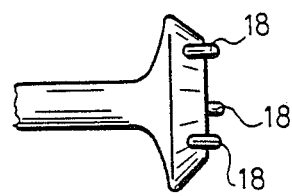
FIG. 11 illustrates the end of the tool for screwing in and out the acetabular unit.
Figure 12:
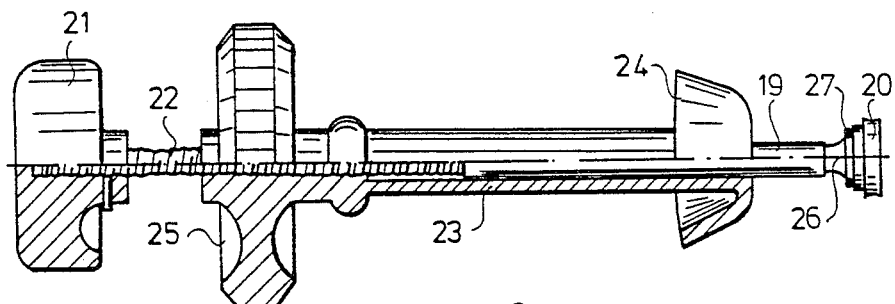
FIG. 12 shows a preferred embodiment of the tool for the implantation of the acetabular basket.

FIGS. 11 and 12 show the tool for the implantation of the acetabular unit according to the invention. By means of the tool according to FIG. 11 the acetabular unit 11 can be screwed into the acetabular basket 1, by means of the pins 18—as already mentioned—fitting into the bores 14.

FIG. 12 presents the tool for implanting and anchoring the acetabular basket in the bone cavity. Said tool contains a shaft, at one end of which a threaded head—part 20 is arranged. This threaded head-part 20 fits into the threaded bore 2 of the acetabular basket 1.

On the other end of the shaft 19 the grip 21 is arranged, immediately before it a screw-thread 22 is formed.

The tubular shaft 23 is pulled onto the shaft 19, on one end of the tubular shaft there is the extruding insert 14 arranged, the other end carries the driving wheel 15. In relation to the tubular shaft 23 the driving wheel 15 can carry out a free rotary motion, in the inside there is an inner thread fitting to the screw-thread 22 of the shaft 19. In such a manner clamping of the shaft 19 and rotation of the driving wheel 15 results in the axial displacement of the extruding insert 14.

Before the threaded head-part 20 the shaft 19 is provided with the neck-part 26 and thereon, between the neck-part 26 and the threaded head-part 20 a rubber ring 27 is arranged.

The acetabular unit construction according to the invention is implanted in the following way.

The acetabular basket having been selected is screwed onto the threaded head-part 20 of the tool.

Figure 13:
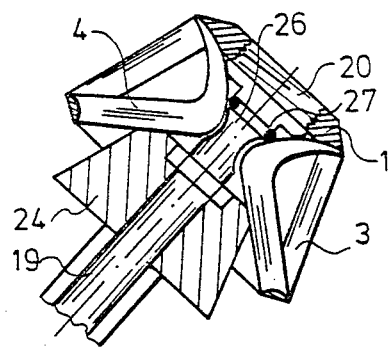
FIG. 13 is the sectional view of the head-part of the tool used for implantation and of the acetabular basket.

Then, the properly chosen anchors 4 are fitted into the cutouts 3, as it is to be seen in FIG. 13. The neck-part 26 of the shaft 19 enables tilting of the anchors 4 into the basic position, while the anchors 4 are kept safely in this position by means of the rubber ring 26.

Figure 14:
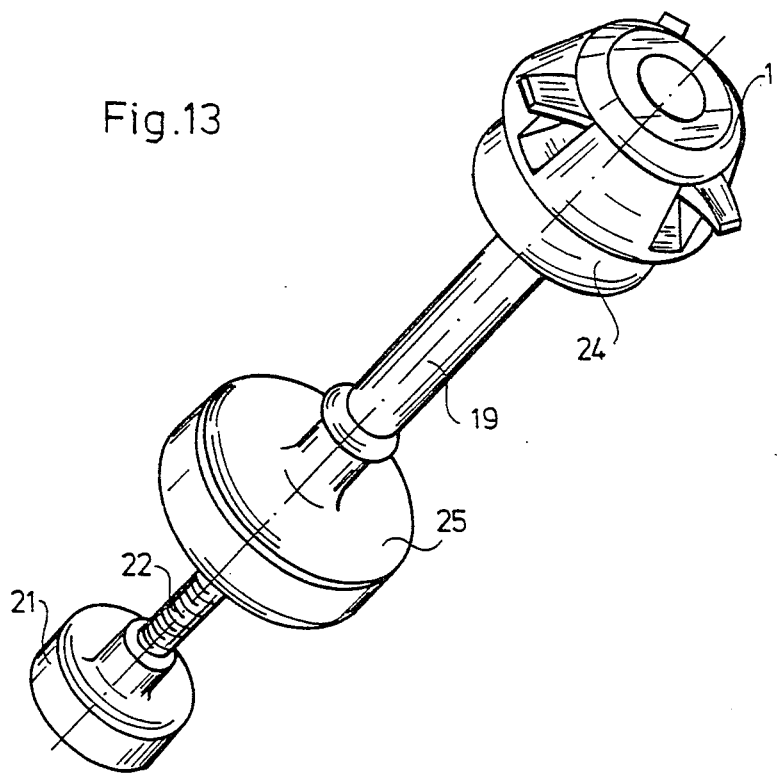
FIG. 14 is the perspective view of the tool according to FIG. 12 with the acetabular basket.

The unit thus assembled is fitted into the cotyloid cavity of the hip-bone having been formed to the proper size with the special tool, and by grasping the grip 21 rotation of the driving wheel 25 is initiated. As it is to be seen in FIG. 14, the extruding insert 24 arranged on the end of the tubular shaft 23 is tilting the anchors 4 gradually outwards. In course of this activity the claws are pressed into the medullary substance of the hip-bone and in such a manner, that their helical bottom face 9 is sort of pulling-in the acetabular basket 1 into the cotyloid cavity.

With the preferred embodiment illustrated here the cutouts 3 and the anchors 4 are arranged on the mantle of the acetabular basket, such that when positioned in a proper way—anchoring is taking place in anatomically defined directions; towards the hip-bone, the ischium and the pubic bone. In these directions, the bone-substance is relatively strong and thick.

As a consequence of the formation of the anchors, as well as of the outer mantle of the acetabular basket the acetabular basket itself is wedged into the cotyloid cavity. After having established the bond, the threaded head-part 20 of the shaft 19 is to be screwed out from the acetabular basket 1, and by using the tool according to FIG. 11 we screw the acetabular unit 11 in its place.

It has been demonstrated in experiments conducted that the construction according to the invention can be implanted in a most simple and quick way, and compared to known solutions, it guarantees a far stronger bond, which again can be easily and quickly released in case of necessity, as previously explained.

The fixing of the acetabular basket by means of the anchors according to the invention results in several accessory advantages. One advantage being that acetabular basket may have an asymmetric design and have a collared flange. Another advantage is that acetabular unit can be arranged eccentrically in the acetabular basket, exchange does not require disassembly of the acetabular basket.

Fixing with the anchors is considered as especially advantegous a so-called shallow acetabulum condition in which the number of the threads which can be formed is low. Safety of anchoring is increased by the fact that the anchors can be optionally arranged, always in compliance with requirements and state of the bone substance.

In spite of these advantages, the construction according to the invention does not exclude simultaneous use with the earlier specified solutions. In case of necessity the mantle of the acetabular basket may be coated with a porous, bioactive material and in course of implantation cement may be also used, however, this is proposed only for extreme cases, when the aim of the construction lies just in the safe machanic anchoring.

Future exchange of the worn insert will be essentially easier, representing a far less involved surgical procedure in comparison to traditional surgical interventions.

As a result of the shortened duration of operating time the number of complications resulting from infection can be also reduced.

Although, only one hip-prosthesis and only some embodiments thereof are presented, for those skilled in the art it is quite obvious that the construction according to the invention can be successfully used for any other prosthesis, utilizing all the advantageous features, as described earlier.

It is also obvious, that the fixing anchors—in addition to the embodiments shown here—can be prepared in several other versions, always in dependence on the prevailing requirements. The anchors can be prepared in a plurality of versions and sizes, accordingly, in every cae the most optimal versions can be used, as the anchors are exchangeable. As already mentioned, in a given case within one prosthesis several anchor types can be used, if diversity is motivated by circumstances.

It is also unambiguous that both the acetabular unit and the acetabular basket may be realized in several embodiments, the same relates to the fixing tool. It should be emphasized that the tool having been specified here does not represent the single possible solution. The construction need not to be anchored with a tool at all. As ina given case the acetabular unit can be formed such (e.g. from a very-hard synthetic material like ceramics, that it is pushing out the anchors. It is also possible to make an acetabular unit which is provided with an external metal bell for facilitating anchoring.

However, the point of the invention is the construction provided with anchors, as specified in the claims, which enables mechanical fixing with the utmost safety.

What we claim is:

1. A mechanically fixable acetabular unit for prostheses comprising:
   (a) an acetabular basket made of biocompatible material having an open face, a curved base and walls defining an interior space;
   (b) cutouts defined by said walls of said acetabular basket;
   (c) L-shaped anchors, having a longer and a shorter shank, positioned within said cutouts in such a manner that said shorter shank is at the portion of the cutout nearest said curved base and said shorter shank is formed as a sharp pointed claw, whereby said L-shaped anchors pivot, said pointed claw on each anchor thus engaging a bone;
   (d) a threaded bore defined by said curved base of said acetabular basket; and
   (e) an acetabular basket insert comprising:
      (i) insert side walls having the same shape as the walls of said acetabular basket defining said interior space;
      (ii) an insert base having the same shape of the curved base of said acetabular basket defining said interior space;
      (iii) a threaded pin, dimensioned, configured and proportioned to matingly engage said threaded bore defined by said curved base, said threaded pin located on said insert base; and
      (iv) a cavity having a hemispherical surface, said inset maintaining said anchors in a pivoted, bone engaging position when said insert is placed in said acetabular basket.

2. An acetabular unit as claimed in claim 1, wherein said cutouts are rectilinear, having a height and a width wherein said height is greater than said within and said height is oriented along a line connecting said open face and said curved base along said walls and a face of said cutout closest to said open face of said acetabular basket is arched.

3. An acetabular unit as claimed in claim 2, wherein the longer shank of said anchors have a face that abuts said face of said cutout closest to said open face of said acetabular basket, said shank face having a trough that may accommodate said arched face of said cutout.

4. An acetabular unit as claimed in claim 1, wherein said anchors have a plurality of claws.

5. An acetabular unit as claimed in claim 1, wherein said claw has several points.

6. An acetabular unit as claimed in claim 1, wherein said claw has a surface provided with grooves.

7. An acetabular unit as claimed in claim 1, wherein said claw has a surface provided with ribs.

8. An acetabular unit as claimed in claim 1, wherein said claw is curved.

9. An acetabular unit as claimed in claim 8, wherein said claw has an outer edge that is curved such that an arc of constant radius is formed.

10. An acetabular unit as claimed in claim 9, wherein face of said cutouts furthest from the open face of said basket is curved such that an arc of the same constant radius of said claw if formed.

11. An acetabular unit as claimed in claim 1, wherein said basket walls defining an interior space define a volume that is substntially a conic section.

12. An acetabular unit as claimed in claim 1, wherein sid contents are uniformly spaced in said basket.

* * * * *